Figure 1:
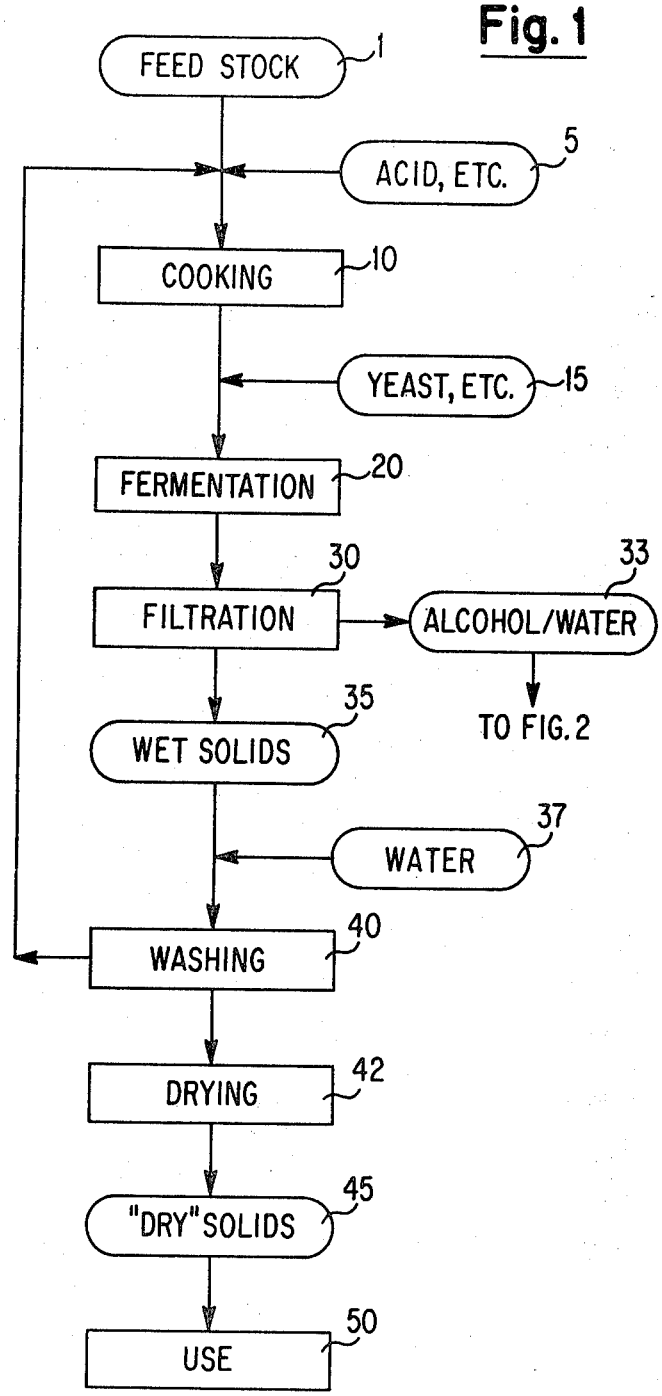

United States Patent [19]

Roth

[11] 4,425,137

[45] * Jan. 10, 1984

[54] ALCOHOL AND FUEL PRODUCTION

[75] Inventor: Ernest R. Roth, Villanova, Pa.

[73] Assignee: Biohol Corporation, Wilmington, Del.

[*] Notice: The portion of the term of this patent subsequent to Dec. 22, 1998 has been disclaimed.

[21] Appl. No.: 331,964

[22] Filed: Dec. 18, 1981

Related U.S. Application Data

[63] Continuation-in-part of Ser. No. 217,703, Dec. 18, 1980, Pat. No. 4,306,884.

[51] Int. Cl.³ .............................................. C10L 1/18
[52] U.S. Cl. .......................................... 44/56; 44/53;
 44/77; 568/913; 568/918; 203/43
[58] Field of Search ............... 44/53, 56, 77; 568/913,
 568/918; 203/43

[56] References Cited

U.S. PATENT DOCUMENTS 4,161,429  7/1979  Baiel .................................... 568/913
4,251,231  2/1981  Baird ....................................... 44/53
4,306,884  12/1981  Roth ....................................... 44/56

Primary Examiner—Jacqueline V. Howard
Attorney, Agent, or Firm—Charles A. McClure

[57] ABSTRACT

Alcohol/water mixtures, such as those produced by fermentation of biomass material, are separated by extraction of alcohol with a solvent, comprising a higher aliphatic alcohol in major amount and an aliphatic hydrocarbon in minor amount, especially suited to such extraction and to subsequent removal. The solvent alcohol desirably has a branched chain, or the hydrocarbon an unsaturated bond, or both. Conventional distillation steps to concentrate alcohol and eliminate water are rendered unnecessary at a considerable reduction in heat energy requirement (usually met with fossil fuel). Optional addition of gasoline between the solvent extraction and solvent recovery steps not only aids the latter separation but produces alcohol already denatured for fuel use.

14 Claims, 2 Drawing Figures

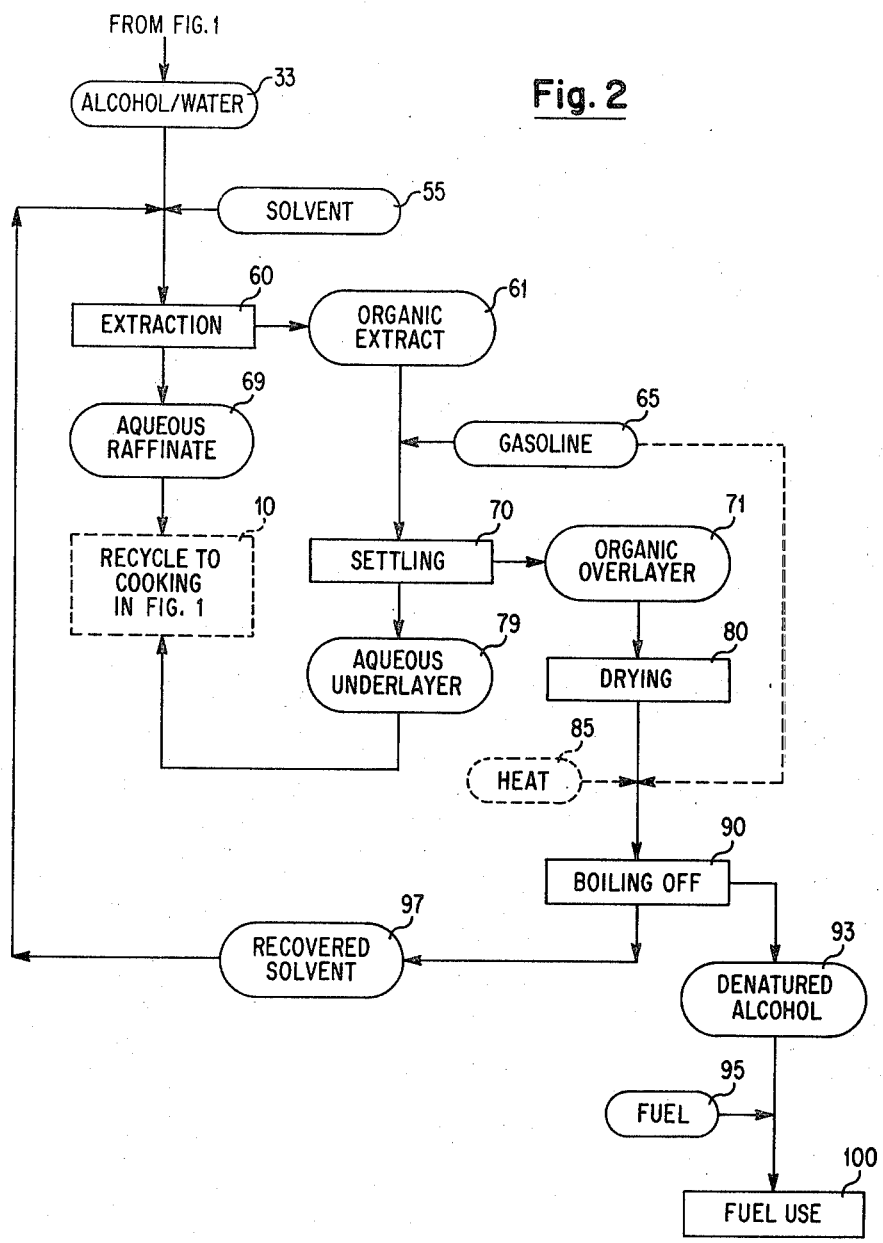

ALCOHOL AND FUEL PRODUCTION

This is a continuation-in-part of application Ser. No. 217,703, filed Dec. 18, 1980, now U.S. Pat. No. 4,306,884.

This invention relates to production of alcohol and fuel by solvent extraction of alcohol/water mixtures at substantial saving in heat energy requirements and in consumption of fossil fuel usually consumed to meet such requirements. The term "alcohol" herein means predominantly "ethanol" unless the context indicates otherwise.

Alcohol/water mixtures, such as those produced by fermentation of biomass material form a single liquid phase, which usually contains more or less equal volumes of ethanol and water, at least after initial distillation, as in a so-called "beer" still. Such mixtures are separated conventionally by further distillation, sometimes with addition of benzene, etc. to yield an anhydrous alcohol fraction, which may contain minor amounts of other alcohols, such as propyl or butyl. Adsorption and solvent extraction are alternative or supplemental methods of separating alcohol and water. An increasing use of alcohol is for fuel, often in admixture with fossil fuels, such as gasoline or even diesel oil, for example, in which anhydrous conditions are favored.

A primary object of the present invention is improved separation of alcohol from alcohol/water mixtures by solvent extraction.

Another object of this invention is reduction of heat energy required in production of alcohol, especially for fuel uses.

Other objects of this invention, together with means and methods for attaining the various objects, will be apparent from the following description and the accompanying diagrams, which are presented by way of example rather than limitation.

FIG. 1 shows schematically production of alcohol/water mixtures, which may be wholly conventional (or not); and FIG. 2 shows schematically the practice of this invention upon such alcohol/water mixtures.

In general, the objects of the present invention are accomplished, in separation of water nd alcohol in a mixture thereof, by extracting alcohol from the mixture with a solvent comprising in major part a higher aliphatic alcohol portion and in minor part an aliphatic hydrocarbon portion. More particularly the alcohol portion contains one or more aliphatic alcohols with from seven to ten carbon atoms per molecule, and the hydrocarbon portion contains one or more aliphatic hydrocarbons with from six to twelve carbon atoms per molecule. An exemplified composition comprises 2-ethyl hexanol and 2-ethyl hexene.

FIG. 1 shows feed stock 1 being subjected to addition of acid, etc. and cooking 10 to degrade and saccharify it. The resulting saccharified material proceeds to fermentation 20 after customary adjustment (not shown) of pH and temperature, followed by addition of suitable yeast, enzymes, etc. 15. The fermentation products are subjected to liquid/solid separation as by filtration 30 to yield alcohol/water mixture 33 and wet solids 35. Water 37 is added for washing 40 of the solids, the wash liquid being recycled to the cooking step, and the washed solids are subjected to drying 42, as by pressing or in vacuum filtration, to produce "dry" (usually rather moist) solids 45 for fuel or other use 50.

FIG. 2 shows addition of solvent 55 to alcohol/water mixture 33 to perform extraction 60. Organic extract layer 61 and aqueous raffinate layer 69 result. The raffinate is recycled to cooking step 10 of FIG. 1 as shown schematically here in broken lines. Gasoline is added optionally (broken line) in minor amount to the organic extract, whereupon aqueous underlayer 79 settles out and can be recycled also to the cooking step of FIG. 1. Indeed, steps 60 and 70 can be performed in prompt succession in a single vessel, if desired, but a more elaborate showing is made here in the interest of clarity.

Organic overlayer 71 resulting as just discussed, is subjected to water-removal or drying 80, as in a molecular sieve or by contact with calcium oxide or with suitable ion-exchange resin or other water-adsorbing medium. Boiling off 60 of the organic layer under mild heating of the resulting anhydrous liquid yields denatured alcohol 93, and leaves recovered solvent 97, which conveniently is recycled to the extraction as indicated. With addition of fuel 95 the denatured alcohol then goes to fuel use 100. The added fuel may be gasoline, usually in a ratio of from 5 to 10 parts per part of denatured alcohol (which optionally already contains about 5% gasoline) to produce what is known as "gasohol". Alternatively, the added fuel can be diesel oil, in similar proportions.

Solvent for use as an extractant in the practice of this invention comprises in major part a higher aliphatic alcohol portion. By "higher" is meant having more carbon atoms per molecule than found in ethanol and the propyl and butyl alcohols often found in association therewith (albeit in minor proportion). The preferred range is from 7 to 10 carbon atoms per molecule. One or more of such higher aliphatic alcohols may be present in that major portion of the solvent.

The extracting solvent also comprises in substantial minor part an aliphatic hydrocarbon, for which the preferred range is from 6 to 12 carbon atoms per molecule. One or more such hydrocarbons may be present in this portion of the solvent.

The constituents of the extracting solvent may have either straight or branched chains, with or without hydrocarbon substituents, and saturated or unsaturated. The solvent alcohol desirably has a branched chain, or the hydrocarbon an unsaturated bond, or both. An example of such solvent, which has given excellent results in the practice of the invention, comprises essentially 4 to 7 parts of 2-ethyl hexanol to 1 part of 2-ethyl hexene, with less than one-half percent of other materials present—some of which may meet the more general requirement for principal components and others of which (e.g., aldehydes) may not but can be tolerated as not deleterious to the process. The preferred solvent major/minor component ratio is about 5 to 1 for 2-ethyl hexanol/2-ethyl hexene.

Other suitable alcohols from which to select include 3,5,5-trimethyl hexanol and isooctyl, nonyl, decyl, and isodecyl alcohols. Other similarly suitable hydrocarbons include mixed trimethyl pentanes, 2,2,5-trimethyl hexane, nonene, decene, and dodecane. Commercially available blends of alcohols in the suitable range may prove satisfactory also, as may commercial hydrocarbon blends. Of course, complete compatibility of any given combination of components in the process of this invention should be assured prior to full-scale operations.

The usual liquid fermentation product or "beer" comprises chiefly water, with the alcohol content being as low as about 5% in the absence of the common pot still, which can raise the alcohol content to about equal the water content. Addition of solvent thereto in a volume up to several times that of the beer extracts the alcohol therefrom, and the extract can be decanted from the heavier aqueous raffinate resulting. With the exemplified solvent, the separation time is as brief as a couple minutes; the extract contains from about 2% to 4% water, and the raffinate contains so little solvent (less than about 1%, usually less than ½%) that it can be recycled repeatedly without excessively adverse influence on the settling time. In comparative tests, similar solvent lacking the hydrocarbon component took on several times as much water and dissolved more into the raffinate, so that separation into two clear continuous phases took progressively longer.

Advantageously in the practice of this invention, gasoline is added to the extract to the extent of about 10% to 20% of the total. This step may be performed either before or after the extract and the raffinate are removed from the extraction vessel (shown afterward in FIG. 2) but in either event additional water settles out of the extract, reducing its water content to less than 1%. Not only does this reduce the burden on an additional drying step to increase the prospective proof but it also adds enough gasoline (about 1 part to 20 parts of alcohol) to denature the resulting fuel alcohol (i.e., render it unfit for beverage purposes).

The rest of the water present is removed conveniently by contact with an adsorbent or other suitably hydrophilic material. One that has proved quite satisfactory in the practice of this invention is an ion-exchange resin of styrene/divinyl benzene type with sulfonic groups for functionality. Examples available commercially are Duolite C-1024 or Amberlite IR-118 from Diamond Shamrock and Rohm & Haas Co., respectively. The resulting essentially anhydrous liquid is then ready to be separated into product and recovered solvent, the latter then being recycled. Optional provision of heat exchange between the hot recovered solvent and water, such as is present in or to be supplied to the cooking step, can cool the solvent and heat the water appropriately.

Some additional benefits of the addition of gasoline to the extract become apparent from the solvent recovery. First, gasoline azeotropes with ethanol and associated alcohols as high as amyl, and with corresponding aldehydes that may be present (in admittedly small amounts) thus both increasing the yield and enabling the solvent to be recycled almost indefinitely; also, the azeotrope boils below the boiling temperature of water, so that the procedure enjoys greater safety and lower heat requirement than in conventional distillation procedures.

Other distillation practices normal in alcohol production (and normally met by combustion of fossil fuels) become unnecessary: such as the customary beer still already mentioned, a rectifying column to produce an alcohol/water azeotrope, an anhydrous column in which benzene or the like is added to eliminate water, and a recovery tower for the benzene. Thus, this invention represents a considerable saving in both cost and resources over wasteful conventional practices. Additional benefits of the invention have been mentioned above, and other advantages will accrue to those who undertake to practice it.

Some variation in the procedures and range in the compositions have been disclosed here also. Optional omission of the disclosed addition of gasoline to the extract would reduce the efficiency of extraction, necessitate further drying if anhydrous product is desired, and require a separate denaturing step for a fuel alcohol product. Where the initial alcohol-to-water ratio substantially exceeds unity, addition of gasoline may be deferred advantageously until after the drying step, as suggested by the alternative broken-line path from gasoline 65 to between steps 80 and 90 in FIG. 2. Other modifications may be made, as by adding, combining, or subdividing parts or steps, while retaining significant advantages of the present invention, which itself is defined in the following claims.

I claim:

1. In separation of a mixture of water and alcohol, the step of extracting alcohol from the mixture by use of a solvent comprising a higher aliphatic alcohol major portion and an unsaturated aliphatic hydrocarbon minor portion.

2. Alcohol/water separation according to claim 1, wherein the solvent alcohol portion is selected from 2-ethyl hexanol, 3,5,5-trimethyl hexanol, and isooctyl, nonyl, decyl, and isodecyl alcohols.

3. In separation of a mixture of water and alcohol, the step of extracting alcohol from the mixture by use of a gasoline free solvent comprising a branched-chain higher aliphatic alcohol major portion and an aliphatic hydrocarbon minor portion.

4. Alcohol/water separation according to claim 3, wherein the hydrocarbon portion is selected from mixed trimethyl pentanes, 2,2,5-trimethyl hexane, 2-ethyl hexene, nonene, decene, and dodecane.

5. In separation of a mixture of water and alcohol, the step of extracting alcohol from the mixture by use of a solvent comprising in major proportion a higher aliphatic alcohol selected from 2-ethyl hexanol, 3,5,5-trimethyl hexanol, and isooctyl, and isodecyl alcohols and in minor proportion an aliphatic hydrocarbon.

6. Alcohol/water separation according to claim 5, wherein the hydrocarbon comprises an alkene.

7. Alcohol/water separation according to claim 6, wherein the alkene is selected from 2-ethyl hexene, nonene, and decene.

8. In separation of a mixture of water and alcohol, the step of extracting alcohol from the mixture by use of a solvent comprising in major proportion a higher aliphatic alcohol and in minor proportion an aliphatic hydrocarbon selected from 2-ethyl hexene, nonene, and decene.

9. Alcohol/water separation according to claim 8, wherein the solvent alcohol is alkyl-substituted.

10. Alcohol/water separation according to claim 9, wherein the solvent alcohol is selected from 2-ethyl hexanol, 3,5,5-trimethyl hexanol, isooctanol, and isodecanol.

11. In separation of a mixture of water and alcohol, the step of extracting alcohol from the mixture by use of a solvent comprising in major proportion a higher aliphatic alcohol and in minor proportion an aliphatic hydrocarbon, wherein the solvent alcohol has a branched chain or the hydrocarbon has an unsaturated bond, or both.

12. Alcohol/water separation according to claim 11, wherein the solvent alcohol is alkyl-substituted and the hydrocarbon contains from 6 to 12 carbon atoms per molecule.

13. Alcohol/water separation according to claim 11, wherein the hydrocarbon is an alkene and the solvent alcohol contains from 7 to 10 carbon atoms per molecule.

14. Alcohol/water separation according to claim 11, wherein the solvent alcohol is alkyl-substituted and the hydrocarbon is an alkene.

* * * * *